United States Patent [19]

Khanna

[11] Patent Number: 4,510,128
[45] Date of Patent: Apr. 9, 1985

[54] RESINATE OF A SUBSTITUTED CARBOXYLIC ACID, THE PREPARATION AND USE THEREOF, AND PHARMACEUTICAL COMPOSITIONS CONTAINING IT

[75] Inventor: Satish C. Khanna, Bottmingen, Switzerland

[73] Assignee: Ciba Geigy Corporation, Ardsley, N.Y.

[21] Appl. No.: 568,976

[22] Filed: Jan. 6, 1984

[30] Foreign Application Priority Data

Jan. 12, 1983 [CH] Switzerland .................. 147/83

[51] Int. Cl.³ ............................................ A61K 31/74
[52] U.S. Cl. ........................................ 424/79; 424/78; 521/32; 525/332.2
[58] Field of Search .................. 428/79, 78; 521/31; 525/332.2

[56] References Cited

U.S. PATENT DOCUMENTS

| | | | |
|---|---|---|---|
| 3,926,864 | 12/1975 | Hodgdon, Jr. | 521/32 |
| 4,058,491 | 11/1977 | Steckler | 521/32 |
| 4,198,395 | 4/1980 | De Simone | 521/32 |
| 4,207,399 | 6/1980 | Kumbara | 521/32 |
| 4,380,590 | 4/1983 | Chong | 521/32 |

OTHER PUBLICATIONS

Chemical Abstracts-141851d, "Antiinflammatory Action of N-(2,6-dichlorophenyl)-O-aminophenylacetic Acid . . . " 1973, Tsurumi et al.
C.A.-16108w, "Structure-Activity Relationships in a Series of Antiinflammatory N-arylantranilic Acids," Kultenbronn et al., 1983.

*Primary Examiner*—Joseph L. Schofer
*Assistant Examiner*—Bernard Lipman
*Attorney, Agent, or Firm*—Michael W. Glynn

[57] ABSTRACT

A resinate of the formula

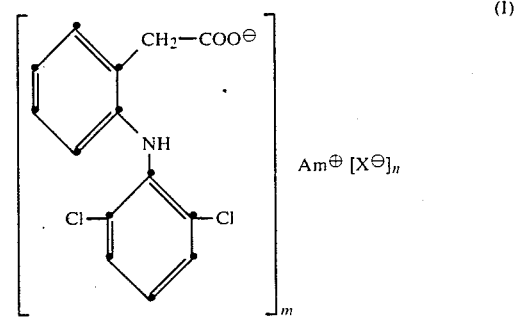

wherein
Am⊕ is a strongly basic copolymer of styrene and divinylbenzene which is in cationic form, said copolymer containing the sum of $m+n$ quaternary ammonium groups and also containing, as main structural unit, the grouping of the formula

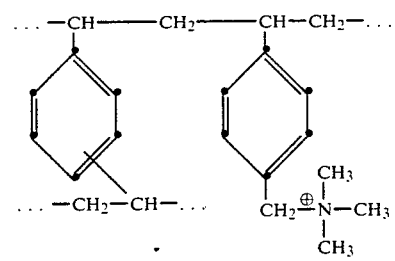

$X^\ominus$ is the anion of an acid different from the anion of the formula

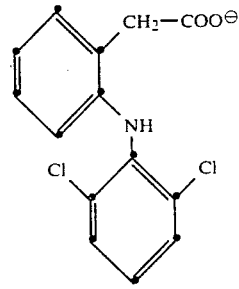

and m and n denote the entire ion capacity of the copolymer, and the molecular weight of which is about $10^7$ to $10^9$, a process for the preparation of said resinate, the use thereof as active ingredient of a drug, and pharmaceutical compositions containing it.

4 Claims, 1 Drawing Figure

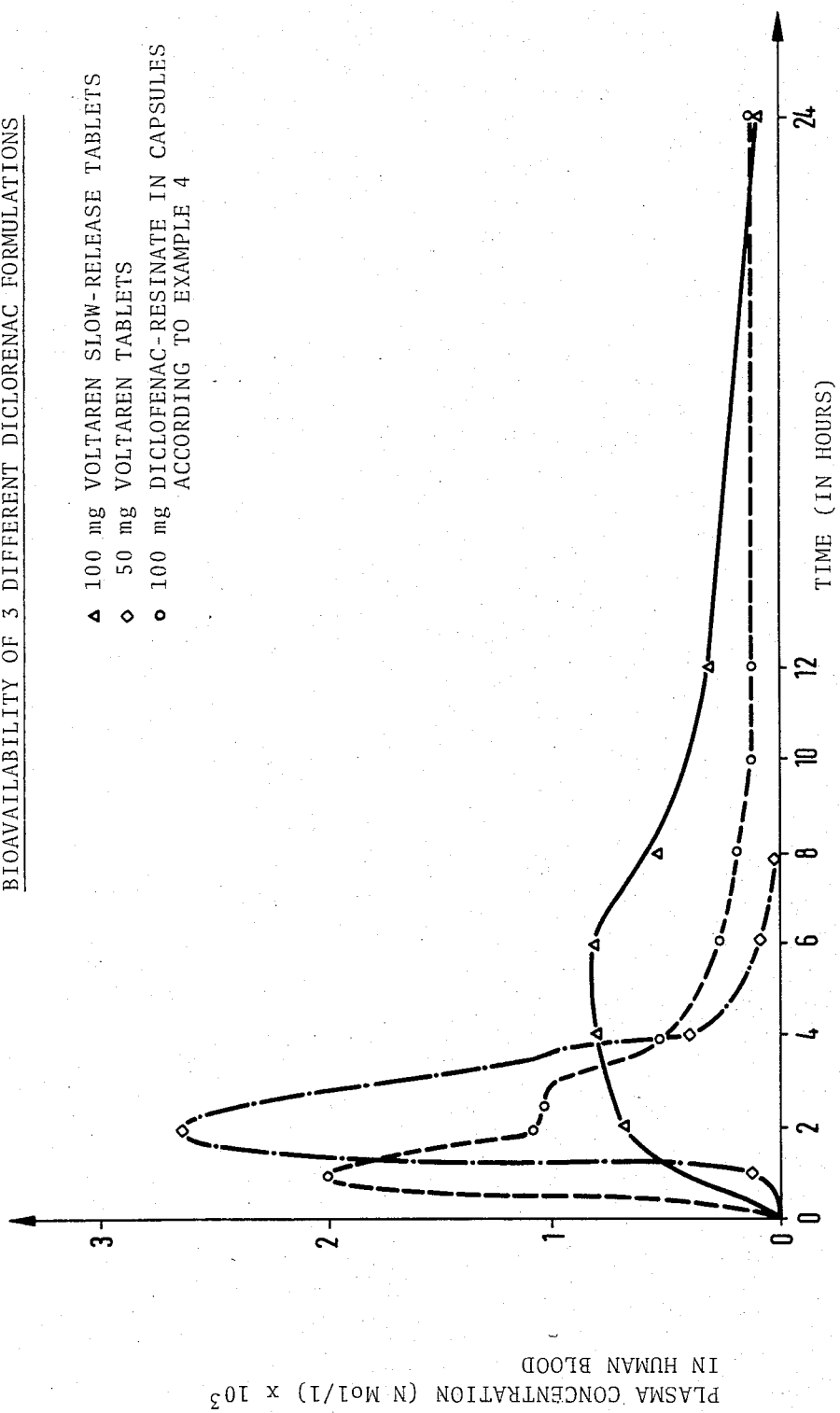

RESINATE OF A SUBSTITUTED CARBOXYLIC ACID, THE PREPARATION AND USE THEREOF, AND PHARMACEUTICAL COMPOSITIONS CONTAINING IT

The present invention relates to the resinate of the formula

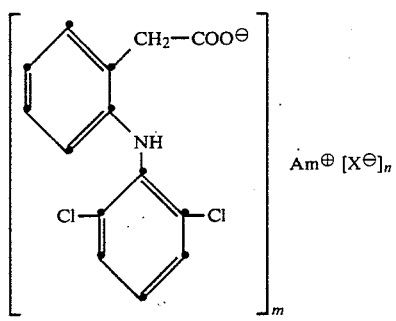

wherein
Am⊕ is a strongly basic copolymer of styrene and divinylbenzene which is in cationic form, said copolymer containing the sum of m+n quaternary ammonium groups and also containing, as main structural unit, the grouping of the formula

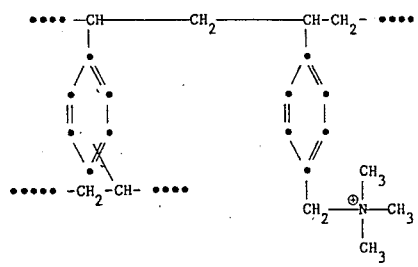

X⊖ is the anion of an acid different from the anion of the formula

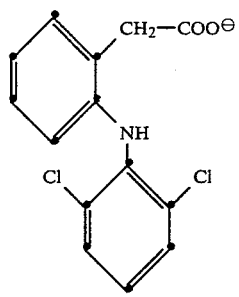

and m and n denote the entire ionic capacity of the copolymer, and the molecular weight of which is about $10^7$ to $10^9$, to a process for the preparation of said resinate, to the use thereof as active ingredient of a drug, and to pharmaceutical compositions containing it.

The o-(2,6-dichloroanilino)phenylacetic acid (diclofenac) contained in the resinate as active ingredient, and especially the sodium salt thereof, is known, as is also its antiinflammatory and analgesic action. The sodium salt is used, for example, as a non-steroid antiinflammatory drug for the treatment of inflammatory conditions. The appropriate drug formulations are administered in particular orally, and also rectally, topically or parenterally.

For various reasons, however, these formulations are not at the present time entirely satisfactory. For example, side-effects are possible when these formulations are administered orally, especially in the upper part of the gastro-intestinal tract. The sodium salt also anaesthetises the mucous membranes of the mouth and tongue and has a bitter taste. These formulations also have a limited duration of action. Further, the active ingredient of the drug, viz. the carboxylic acid, which is released in the stomach, is only poorly water-soluble. Depending on the stomach contents, this poor water-solubility results in a more or less slow and irregular reabsorption.

With the use of the novel resinate of the formula I it is possible to eliminate, or at least substantially to reduce, these and other known shortcomings of the sodium o-(2,6-dichloroanilino)phenylacetate employed in practice up to now. Thus the resinate of this invention is much easier to administer orally, as it is virtually tasteless compared with the sodium salt. The neutralisation of taste in the mouth is best achieved if the stoichiometric ratio of active ingredient to ion exchange resin is about 1:2. The preferred rate of release is achieved, however, with a ratio of 1:1. Although the novel resinate of the formula I has all the desired pharmacological properties of the known sodium salt in at least the same potency, its specific advantages make it substantially more suitable for oral and rectal administration. Thus the active ingredient released from the resinate is reabsorbed mainly in the alkaline part of the intestinal tract, where it is released from the resinate in the form of readily soluble salts and not as a poorly water-soluble acid.

Surprisingly, it has also been found that this active ingredient has a most desirable quick-slow release effect compared with the known prior art formulations, i.e. an initial rapid release of drug is followed by a slow and gradually diminishing release. Moreover, the release of the drug from the resinate is, surprisingly, almost independent of the ionic strength in the gastro-intestinal tract, i.e. of its contents, which can vary depending on the time of day and on eating habits. The advantageous drug release is evident from the table.

The rate of release can also be influenced by the granular size of the resin. The larger the particles the slower the rate of drug release. The preferred particle size is from 20 to 200 μm, preferably from 40 to 100 μm, and the crosslinkage is from 2 to 8%, preferably from 2 to 4%. It is preferred to use USP quality as cholestyramine resin.

Accordingly, the resinate of the formula I is most suitable for use as antiinflammatory agent and as analgesic for oral or rectal administration.

The invention also relates to a process for the preparation of the novel resinate of the formula I, which process can be carried out by methods which are known per se.

A preferred process variant comprises, for example, reacting o-(2,6-dichloroanilino)phenylacetic acid of the formula

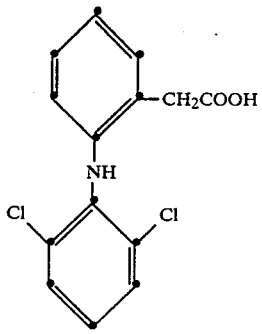

(II)

or a salt thereof, preferably with at least the equimolar amount of a resin of the formula $[Am^{\oplus}][OH^{\ominus}]_{m+n'}$ or a salt thereof with an acid, preferably with a mineral acid.

Anion exchange resins which are suitable for use in the process of the invention are in particular cholestyramine as marketed by Diamond Shamrock e.g. under the registered trademark Duolite ® A 101D, A 101 D/U, A 102D, A 113, A 116, A 143, A 161, A 162 and ES 132, or by Rohm and Haas under the registered trademark Amberlite ® XE 268 P, and which have a degree of polymerisation of $10^8$.

Suitable salts of the acid of the formula II are in particular salts with bases which can be removed from the reaction mixture, for example inorganic salts such as alkali salts.

The invention further relates to pharmaceutical compositions which contain the resinate of the formula I and to a process for the preparation of such compositions. This process comprises mixing the resinate of the formula I with conventional carriers and/or adjuvants and processing the mixture so obtained to a galenic formulation.

Specifically, the invention relates to the pharmaceutical compositions described in the Examples and to the preparation thereof.

The pharmaceutical compositions which contain the resinate of the formula I are those for enteral, e.g. oral or rectal, administration.

The novel pharmaceutical compositions are preferably those for enteral administration, e.g. unit dosage forms such as oral and rectal formulations, e.g. dragées, tablets, capsules, syrups, drops, suppositories or rectal capsules.

The pharmaceutical compositions of the present invention are prepared in a manner known per se, for example by conventional mixing, granulating, confectioning, dissolving or lyophilising methods. For example, pharmaceutical compositions for oral administration can be obtained by combining the resinate-drug complex with solid carriers, optionally granulating a resulting mixture and processing the mixture or granulate, if desired or necessary after the addition of suitable adjuncts, to tablets or dragée cores.

Suitable carriers are in particular fillers such as sugar, for example lactose, saccharose, mannitol or sorbitol, cellulose preparations and/or calcium phosphates, e.g. tricalcium phosphate or calcium biphosphate, and also binders such as starch pastes, e.g. maize, corn, rice or potato starch, gelatin, tragacanth, methyl cellulose and/or polyvinylpyrrolidone, and/or, if desired, disintegrators, such as the above-mentioned starches, also carboxymethyl starch, crosslinked polyvinylpyrrolidone, agar, alginic acid or a salt thereof such as sodium alginate. Adjuncts are in particular glidants and lubricants, for example silica, talc, stearic acid or salts thereof such as magnesium stearate or calcium coatings which can be resistant to gastric juices, using inter alia concentrated sugar solutions which may contain gum arabic, talc, polyvinylpyrrolidone, polyethylene glycol and/or titanium dioxide. Dyes or pigments can be added to the tablets or dragée coatings, for example to identify or indicate different doses of active ingredient.

Further pharmaceutical compositions for oral administration are dry-filled capsules made of gelatin and also soft sealed capsules consisting of gelatin and a plasticiser such as glycerol or sorbitol. The dry-filled capsules can contain the active ingredient in the form of granules, for example in admixture with fillers such as lactose, binders such as starches, and/or glidants such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers can also be added.

Oral formulations are also drinkable suspensions in the form of syrups.

As the resinate of this invention decomposes to a slight degree during processing and storage, even in the form of a pharmaceutical composition, accompanied by the formation of very dilute malodorous aliphatic amines, it is advantageous to add deodorising substances to the resinate. Particularly suitable deodorising substances are activated carbon or styrene/divinyl cation exchangers containing sulfonic acid or carboxyl groups (q.v. GDR patent specification No. 147 819).

Suitable pharmaceutical compositions for rectal administration are e.g. suppositories, which consist of a combination of the active ingredient with a suppository base. Examples of suitable suppository bases are natural or synthetic triglycerides, paraffin hydrocarbons, polyethlyene glycols and higher alkanols. It is also possible to use gelatin rectal capsules which contain a combination of the active ingredient with a base material. Suitable base materials are e.g. liquid triglycerides, polyethylene glycols and paraffin hydrocarbons.

The present invention also relates to the use of the resinate of the formula I, preferably for the treatment of inflammatory conditions, most preferably for the treatment of chronic inflammatory diseases of the rheumatic type, especially chronic arthritis.

The following Examples illustrate the invention, but are not intended to limit its scope in any way. Pressures are indicated in mbars.

EXAMPLE 1

Conditioning of the resin: 100 g of cholestyramine (Duolite 143) with a particle size of 40 or 80 μm are suspended in 500 ml of 2N sodium hydroxide. The mixture is stirred for 4 hours at 50° C. The supernatant solution is decanted and the resin is washed 4 times with deionised water. Then 500 ml of 2N hydrochloric acid are added and the mixture is again stirred for 4 hours at 50° C. The supernatant liquid is again decanted and the resin is washed with an excess of hot deionised water until the pH of the decanted solution is between 8 and 9. The resin is then suspended for 2 hours in isopropanol to remove any possible organic impurities. The resin is then filtered and washed twice with deionised water and subsequently dried to constant weight at 50° C. in vacuo.

(a) Loading the resin with active ingredient: 100 g of diclofenac sodium are dissolved in 5 l of deionised water and then 100 g of conditioned cholestyramine (80 μm) are slowly dispersed in this solution. The mixture is stirred for about 12 hours at 50° C. The resinate-drug complex so obtained is isolated by filtration and dried to constant weight at 50° C. in vacuo.

(b) Loading the resin with active ingredient: 100 of diclofenac sodium are dissolved in 5 l of deionised water and then 200 g of conditioned cholestyramine (40 μm) are slowly dispersed in this solution. The mixture is stirred for about 12 hours at 50° C. The resinate-drug complex so obtained is isolated by filtration and dried to constant weight at 50° C. in vacuo.

EXAMPLE 2

Tablets containing 150 mg of diclofenac sodium can be prepared as follows:

| Composition (for 1000 tablets) | |
|---|---|
| resinate-drug complex obtained in Example 1a | 300.0 g |
| lactose | 100.7 g |
| corn starch | 7.5 g |
| polyethylene glycol 6000 | 5.0 g |
| talcum | 5.0 g |
| magnesium stearate | 1.8 g |
| demineralised water | q.s. |

Preparation: All the solid ingredients are first passed through a 0.6 mm sieve. The resinate-drug complex, the lactose, the magnesium stearate and half of the starch are then mixed. The remaining half of the starch is suspended in 40 ml of water and this suspension is added to a boiling solution of the polyethylene glycol in 100 ml of water and mixed with the above mixture. The composition so obtained is granulated, if necessary with the addition of water. The granulate is dried overnight at 35° C., passed through a 1.2 mm sieve and compressed to domed tablets of 8 mm diameter.

EXAMPLE 3

Tablets containing 150 mg of diclofenac sodium can be prepared as follows:

| Composition (for 20,000 tablets) | |
|---|---|
| resinate-drug complex obtained in Example 1a | 3000.0 g |
| lactose (ground) | 350.0 g |
| colloidal silica | 30.0 g |
| polyvinylpyrrolidone | 30.0 g |
| microcrystalline cellulose | 400.0 g |
| corn starch | 690.0 g |
| Zerolite 236 SRC 48 | 100.0 g |

Preparation: All the solid ingredients are first passed through a 0.6 mm sieve and then the active ingredient is mixed with all the adjuvants. The final tablet composition is then compressed to tablets of 9 mm diameter having a weight of 230 mg.

EXAMPLE 4

2000 g of resinate-drug complex obtained in Example 1a are filled into 10,000 capsules (size 1). Each capsule contains 100 mg of active ingredient.

EXAMPLE 5

3000 g of resinate-drug complex obtained in Example 1a are thoroughly mixed with 10 g of activated carbon and the mixture is passed through a 0.6 mm sieve. The mixture is then filled into 10,000 capsules (size 1). Each capsule contains 150 mg of active ingredient.

EXAMPLE 6

20 g of tragacanth, 6 g of methyl p-hydroxybenzoate and 1.5 g of propyl p-hydroxybenzoate are dissolved in 2 l of water at 80°–90° C. The resultant gel is cooled and 75 g of the dry resinate-drug complex obtained in Example 1b and 5 g of Zerolite 225 (50μ) are added and the mixture is thoroughly dispersed using a homogeniser. Then 2000 g of 70% sorbitol solution are added. The dispersion is then bulked with water to a final volume of 5 liters, so that the resultant suspension contains about 1.5% of resinate. A teaspoonful of this suspension approximately contains a dose corresponding to 50 mg of diclofenac sodium. This dose is contained exactly in 5 ml of suspension.

EXAMPLE 7

3 g of the diclofenac resinate obtained in Example 1a are suspended in a melt of a 1:1 mixture of 20 g of polyethylene glycol 4000 and polyethylene glycol 1000. The melt composition so obtained is poured into suppository moulds and then cooled. Each rectal suppository weighs about 2 g and has an active ingredient content corresponding to 150 mg of diclofenac sodium.

EXAMPLE 8

60 g of Duolite A 161 (average particle size 80 μm) are suspended in 1 liter of 1.5N sodium hydroxide and the suspension is heated on a water bath to 50° C. After 4 to 5 hours the suspension is filtered and the filtrate is washed with deionised water. The resin so obtained is suspended in 1 liter of 2N hydrochloric acid and the suspension is stirred at 50° C. for 4 to 5 hours. The resin is isolated by filtration and the filtrate is washed with deionised water. The above steps are repeated twice. The resin is suspended in isopropyl alcohol and the suspension is stirred for 4 to 5 hours. The resin is isolated by filtration and dried in vacuo at 50° C. 15 g of diclofenac sodium are dissolved in 1 liter of deionised water. Then 15 g of the activated resin are suspended in the above solution and the suspension is stirred for 12 hours. The resinate is then isolated by filtration and dried in vacuo at 50° C. Tablets, capsules, suspensions and suppositories are prepared from this resinate in accordance with the particulars described in Examples 2 to 6.

What is claimed is:

1. A resinate of the formula

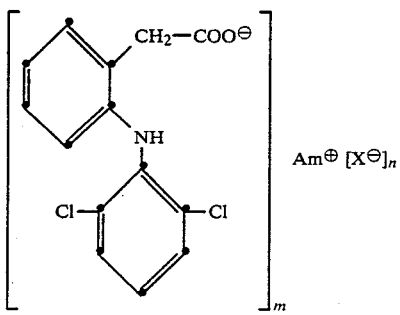 $Am^{\oplus} [X^{\ominus}]_n$  (I)

wherein

Am⊕ is a strongly basic copolymer of styrene and divinylbenzene which is in cationic form, said copolymer containing the sum of m+n quaternary ammonium groups and also containing, as main structural unit, the grouping of the formula

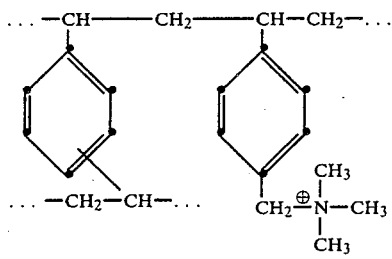

$X^{\ominus}$ is the anion of an acid different from the anion of the formula

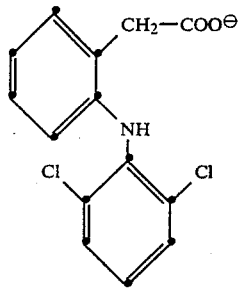

and m and n denote the entire ionic capacity of the copolymer.

2. A resinate according to claim 1, wherein the stoichiometric ratio of active ingredient to ion exchange resin is 1:1 to 1:2.

3. A pharmaceutical composition suitable for administration to mammals for the treatment of inflammation and pains, comprising an effective amount of the resinate of the formula I according to claim 1 in combination with one or more pharmaceutically acceptable carriers.

4. A method for treating inflammation and pains in mammals which comprises administering to a mammal in need thereof an effective amount of the composition of claim 3.

* * * * *